United States Patent [19]

Nagasawa et al.

[11] 4,281,181
[45] Jul. 28, 1981

[54] NOVEL L-γ-GLUTAMYL-3-CARBOXY-4-HYDROXYANILIDE AND SALTS THEREOF

[75] Inventors: Takeshi Nagasawa; Katsumasa Kuroiwa; Katsuyuki Takabayashi, all of Koriyama; Norimasa Takizawa, Funabashi; Kazuyo Hagihara, Ichikawa; Tadami Akatsuka, Tsuchiura, all of Japan

[73] Assignees: Nitto Boseki Co., Ltd., Fukushima; Iatron Laboratories, Inc., Tokyo, both of Japan

[21] Appl. No.: 94,072

[22] Filed: Nov. 14, 1979

[30] Foreign Application Priority Data

Nov. 16, 1978 [JP] Japan .................. 53-141463

[51] Int. Cl.$^3$ ........................... C07C 101/72
[52] U.S. Cl. ..................... 562/453; 560/46; 424/8
[58] Field of Search ............... 562/455, 453, 448, 564, 562/563; 560/46

[56] References Cited

U.S. PATENT DOCUMENTS 3,383,411  5/1968  Schultz et al. ............ 562/455
3,452,086  6/1969  Montzka ................. 562/455

OTHER PUBLICATIONS

Ross et al., J. Med. Chem., vol. 6, pp. 208-210, (1963).
Lloyd et al., J. Med. Chem., vol. 8, pp. 398-400, (1965).
Lingens et al., Justis Libig, #702, pp. 169-179 (1967).
Mori et al., Chem. Abst., vol. 89, #191303w (1978).

Primary Examiner—Howard T. Mars
Assistant Examiner—James H. Reamer
Attorney, Agent, or Firm—Norbert P. Holler; James J. Long

[57] ABSTRACT

Novel L-γ-glutamyl-3-carboxy-4-hydroxyanilide of the formula,

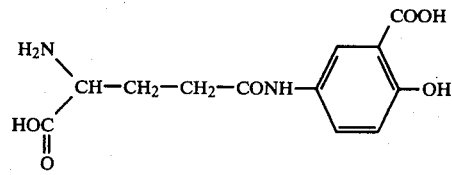

an acid addition salt thereof, or an alkali metal or amine salt thereof, which is useful for determining the activity of γ-glutamyl transpeptidase.

1 Claim, 1 Drawing Figure

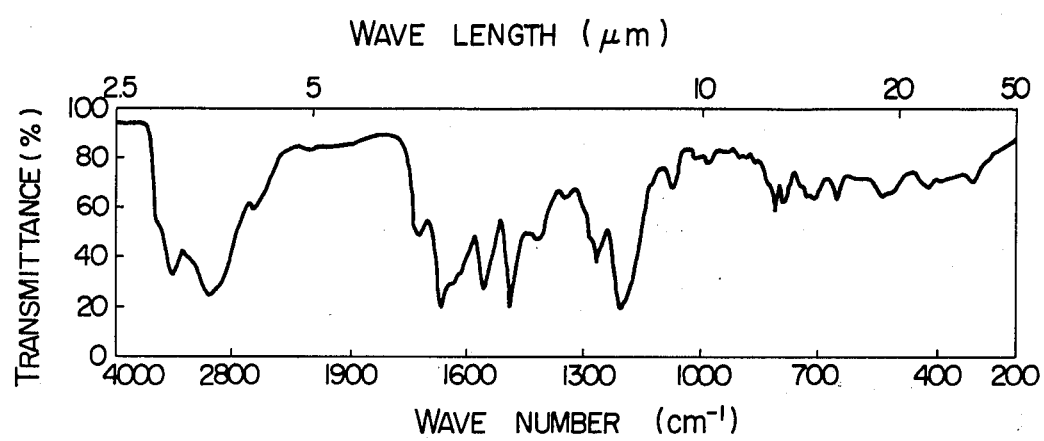

NOVEL L-γ-GLUTAMYL-3-CARBOXY-4-HYDROXYANILIDE AND SALTS THEREOF

This invention relates to a novel compound L-γ-glutamyl-3-carboxy-4-hydroxyanilide, an acid addition salt thereof, or an alkali metal or amine salt therof. It relates also to a method for determining the activity of γ-glutamyl transpeptidase by the use of said novel compound or a salt thereof and to a method for preparing said novel compound or a salt thereof.

As known well, γ-glutamyl transpeptidase (hereinafter referred to simply as γ-GTP) is an enzyme capable of hydrolyzing a γ-glutamylpeptide as well as transferring the γ-glutamyl radical to other peptides, amino acids, or the like. This enzyme is widely distributed in living tissues and in blood sera. The γ-GTP content of a patient's serum has been known to vary markedly with the type of underlying disease.

The γ-GTP content is very high in the serum of a patient suffering from cholangiolitic hepatitis, obstructive jaundice, or primary or metastatic hepatoma. Chronic hepatitis increases the serum γ-GTP content when it is in the active state, whereas the content remains in a low level when the disease is in inactive state. In general, the variation in the serum γ-GTP level is specific to chronic diseases of liver and is of diagnostic significance entirely different from that of leakage enzyme. Therefore, the assay of the activity of serum γ-GTP has become an indispensable test for the diagnosis of the above-noted diseases and for the comprehension of the condition of each disease.

For the assay of γ-GTP activity, there had been proposed several methods in which synthetic substrates are employed and the formed amine compounds are determined. However, since all of these methods revealed merits and demerits, development of a new synthetic substrate has been awaited. For instance, in one of the above proposed methods, γ-glutamyl-α-naphthylamide is used as the substrate and the formed α-naphthylamine is colorimetrically determined after conversion to a diazonium salt [Clinica Chimica Acta, Vol. 7, 755 (1962)]. This method proved to be unpractical, because naphthylamine was known to be carcinogenic and the procedure was complicated and time-consuming. In another proposed method, γ-glutamyl-p-nitroanilide is used as substrate to determine colorimetrically p-nitroaniline, yellow in color, which is formed from the substrate [Clinica Chimica Acta, Vol. 65, 21 (1975)]. This method required a precise blank test for each serum sample in order to avoid the influence of serum ingredients and the results of assay were inaccurate. The colorimetric determination of p-nitroaniline after condensation with p-dimethylaminocinnamaldehyde presented such a problem that the color development sensibility is greatly affected by temperature, resulting in insufficient reproducibility. In another procedure, p-nitroaniline is diazotized, then condensed with 3,5-xylenol, and the red color thus developed is colorimetrically measured [Japanese Patent Application Laid-open ("Kokai"), No. 32092/78]. This procedure was found to be not sufficiently simple, because multiple steps are involved in the treatment of p-nitroaniline. Recently, an attempt was made to assay the γ-GTP activity by using γ-glutamyl-p-dimethylaminoanilide as the substrate and determining colorimetrically the formed p-dimethylaminoaniline after color development with a pentacyano iron complex [Japanese Patent Application Laid-open ("Kokai"), No. 146,693/77]. This method has disadvantages in that the shelf life of the color developer solution is only several days owing to insufficient stability and the amount of cyan liberated in waste water might give rise to environmental pollution. Moreover, all of the above-noted substrates show poor solubility in water and necessitate the use of a solubilizing agent such as surface active agent, organic solvent, or the like, which is not easily controllable. Even when such an agent is used, the concentration is often not sufficient for the reaction.

An object of this invention is to provide a substrate for use in the assay of γ-GTP activity, which has sufficient solubility in water and properties capable of overcoming the difficulties encountered by the prior art in practicability, safety, accuracy, reproducibility, simplicity, stability, and possibility of environmental pollution.

Another object of this invention is to provide a method for assaying the γ-GTP activity, which comprises the use of the said substrate.

Further, an object of the invention is to provide a method for producing said substrate.

The present inventors conducted studies on the improvement of conventional methods for the assay of γ-GTP activity which have aforementioned disadvantages. As a result, they found a novel substrate having excellent properties. Based on the finding, the present invention has been accomplished.

This invention relates to L-γ-glutamyl-3-carboxy-4-hydroxyanilide represented by the formula

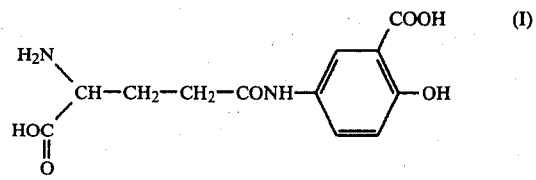

(I)

an acid addition salt thereof, or an alkali metal or amine salt thereof, which is useful as the substrate for use in the assay of γ-GTP activity. As is apparent from the foregoing description, the use of the compound of this invention is in the assay of γ-GTP activity. In performing the assay, the substrate of this invention is allowed to react with γ-GTP of a serum in a buffer solution of pH 7.5 to 9.5 and the 3-carboxy-4-hydroxyaniline formed by the reaction is allowed to undergo oxidative condensation with a suitable coupler to form a colored substance which is then determined colorimetrically to asssay the γ-GTP activity of the serum.

Suitable couplers for the development of color in acidic side are aniline compounds such as, for example, N,N-diethylaniline and those for the development of color in alkaline side are phenol and naphthol compounds such as, for example, 2,6-xylenol and 2,5-xylenol.

The oxidizing agent most suitable for use in the above oxidative condensation is sodium metaperiodate, though various others such as hydrogen peroxide, persulfates and the like can be used.

The colored substance formed by the oxidative condensation between 3-carboxy-4-hydroxyaniline and a coupler shows a maximum absorption in a broad wave length range of from 560 to 770 nm depending on the type of coupler. The color development is very steady, affected very little by the change in temperature and, hence, is suited for the assay of γ-GTP activity.

Since the compound L-γ-glutamyl-3-carboxy-4-hydroxyanilide has hydrophilic functional groups, it is easily soluble in water without necessitating a solubilizing agent such as surface active agent or organic solvent. Therefore, the preparation of reagents and the procedure of measurement are both easily manageable and the substrate can be used in a concentration sufficiently high for the reaction. These are major advantages of this invention.

Further, as one of the features of this invention, the assay of γ-GTP activity is scarcely affected by the presence of impurities in the sample taken from a living body. This is because the assay according to this invention is conducted at a wave length longer than 560 nm, as contrasted to the L-γ-glutamyl-p-nitroanilide method in which the measurement is carried out at a wave length shorter than 560 nm. Accordingly, no blank test is necessary for each sample, permitting of rapid assay. The reducing substances such as uric acid and ascorbic acid in the sample are decomposed by an excess of oxidizing agent and, hence, have no effect on the accuracy of the measurement.

From the foregoing description, it is apparent that as a substrate for the assay of γ-GTP activity, the compound of this invention is far superior to the conventional substrates. As will be shown in the test example described hereinafter, satisfactory correlation exists between the observed values obtained by using the compound of this invention and those obtained by a conventional method widely used heretofore.

The compound of this invention represented by the formula I is prepared in a customary way.

For example, it can be prepared by allowing glutamic anhydride having its amino groups protected to react with 3-carboxy-4-hydroxyaniline and then removing the protective group from the reaction product.

The suitable protective groups include those easily removable under the mild conditions adoptable in the customary peptide synthesis, such as, for example, phthalyl group removable by hydrazine, tert-butoxycarbonyl group and formyl group both removable under weakly acidic conditions, trifluoroacetyl group removable under weakly alkaline conditions, and benzyloxycarbonyl group removable by hydrogen bromide or catalytic reduction. The condensation is easily effected by heating in a suitable solvent such as an inert organic solvent. If necessary, the free amino acid anilide freed from the protective group can be converted to a salt by the addition of various inorganic or organic acids or to an alkali metal salt by the reaction with an alkali compound or to an amine salt.

The invention is illustrated below in detail with reference to Test Example and Example, but the invention is not limited to those examples.

TEST EXAMPLE

Example of the assay for γ-GTP activity in a serum by use of a 2,6-xylenol-sodium metaperiodate developer solution.

In 80 ml of water, were dissolved 0.5 g of glycylglycine and 1.3 g of tris(hydroxymethyl)aminomethane. The solution was adjusted to pH 8.2 with 3N hydrochloric acid and made up to 100 ml by the addition of water to prepare a buffer solution. A substrate buffer solution was obtained by dissolving 113 mg of L-γ-glutamyl-3-carboxy-4-hydroxyanilide in the above buffer solution.

To a test tube containing 1.0 ml of the substrate buffer solution and kept at 37° C., was added 0.02 ml of a serum sample. After 20 minutes of incubation, the mixture was admixed with 3.0 ml of a stopper with color reagent prepared by dissolving 86 mg of 2,6-xylenol and 32 mg of sodium metaperiodate in 100 ml of 0.2 N aqueous potassium hydroxide solution. The resulting mixture was left standing for 10 minutes at room temperature and the absorbance at 615 nm was measured. A blank test was carried out in the same manner as mentioned above, except that 0.02 ml of water was used in place of the serum. The serum γ-GTP activity value was calculated from the difference in absorbance obtained by the above two measurements and the absorbance of 0.02 ml of a standard solution containing a known amount of 3-carboxy-4-hydroxyaniline treated in the same manner as mentioned above.

In the following table, are shown for comparison the measured values thus obtained and those obtained by the dominantly used conventional method which utilizes L-γ-glutamyl-p-nitroanilide as the substrate.

The measured values obtained by the method of this invention were plotted on the ordinate and those obtained by the L-γ-glutamyl-p-nitroanilide method on the abscissa to obtain the following regression equation:

$$y = 1.07x - 1.50.$$

The correlation was satisfactory, the correlation coefficient having been $\gamma = 0.992$.

TABLE

Comparison of measured values obtained by the method of this invention and those obtained by the L-γ-glutamyl-p-nitroanilide method using a human serum.

| Sample No. | Method of this invention | γ-Glutamyl-p-nitroanilide method |
|---|---|---|
| 1 | 205 | 209 |
| 2 | 58 | 58 |
| 3 | 206 | 196 |
| 4 | 529 | 495 |
| 5 | 91 | 81 |
| 6 | 85 | 114 |
| 7 | 144 | 143 |
| 8 | 53 | 49 |
| 9 | 32 | 31 |
| 10 | 9 | 9 |
| 11 | 22 | 19 |
| 12 | 21 | 19 |
| 13 | 6 | 6 |
| 14 | 11 | 11 |
| 15 | 10 | 10 |
| 16 | 62 | 61 |
| 17 | 26 | 26 |
| 18 | 21 | 20 |
| 19 | 7 | 9 |
| 20 | 5 | 7 |
| 21 | 72 | 60 |
| 22 | 326 | 289 |
| 23 | 164 | 142 |
| 24 | 392 | 354 |
| 25 | 13 | 14 |
| 26 | 16 | 17 |
| 27 | 22 | 20 |
| 28 | 42 | 40 |
| 29 | 8 | 8 |
| 30 | 17 | 16 |
| 31 | 9 | 8 |
| 32 | 9 | 9 |
| 33 | 13 | 14 |

EXAMPLE 1

Synthesis of L-γ-glutamyl-3-carboxy-4-hydroxyanilide.

To a mixture of 25.9 g (0.1 mole) of phthaloylglutamic anhydride and 15.3 g (0.1 mole) of 3-carboxy-4-hydroxyaniline, was added 60 ml of acetic acid. The mixture was allowed to react by heating at 60° C. with stirring for 30 minutes. After completion of the reaction, the reaction mixture was cooled to room temperature and poured into 500 ml of ether, left standing with cooling for 2 hours, and the precipitates were removed by filtration through a glass filter. The filtrate was added slowly with stirring to one liter of n-hexane, placed in a separable flask of 2 liters capacity. The precipitates which were formed were collected by filtration, washed with n-hexane, and dried in vacuo to obtain 41.0 g (99.5%) of crude phthaloyl-L-γ-glutamyl-3-carboxy-4-hydroxyanilide. The crude substance was dissolved in 431 ml of methanol, admixed with 26.8 ml of 100% hydrazine hydrate, and allowed to react at room temperature for 24 hours to remove the phthalyl group. The precipitates which were formed were removed by filtration, and the filtrate was evaporated completely. The residue was dissolved in 212 ml of water and filtered. The filtrate was adjusted to pH 1-2 and left standing overnight. The precipitates which were formed were collected by filtration, washed with water and acetone, and dried in vacuo. Yield: 11.5 g (41%); melting point: 175°-177° C. (decomp.); specific rotation: $[\alpha]_D^{20} = +8.6$ (C=1 0.05 N-NaOH).

Elementary analysis:
$C_{12}H_{14}N_2O_6 \cdot \frac{1}{2}H_2O$ (molecular weight 288.3)

|  | C % | H % | N % |
|---|---|---|---|
| Found: | 49.78 | 4.90 | 9.69 |
| Calculated: | 50.00 | 5.13 | 9.71 |

EXAMPLE 2

Synthesis of L-γ-glutamyl-3-carboxy-4-hydroxyanilide hydrochloride.

2.0 G (7 m mole) of L-γ-glutamyl-3-carboxy-4-hydroxyanilide (I) (molecular weight 282.25) was suspended in 11.25 ml of methanol, and then dissolved by adding thereto 4.2 ml of 2 N hydrochloric acid/acetic acid. While filtrating the solution, the filtrate was poured into 150 ml of ether to precipitate crystals thereof. After cooling over night, the crystals were collected by filtration, thoroughly washed with ether and dried under reduced pressure on a mixture of phosphorus pentoxide and potassium hydroxide at room temperature to give L-γ-glutamyl-3-carboxy-4-hydroxyanilide hydrochloride (molecular weight 318.75). Yield: 1.6 g (71%); melting point: 168°-179° C. (decomposed); specific rotation: $[\alpha]_D^{20} = +20.2$ (C=1, MeOH). Infrared absorption spectrum thereof is as shown in the drawing.

The hydrochloride is better than its free compound in the solubility in buffer solution.

What is claimed is:

1. L-γ-glutamyl-3-carboxy-4-hydroxyanilide represented by the formula

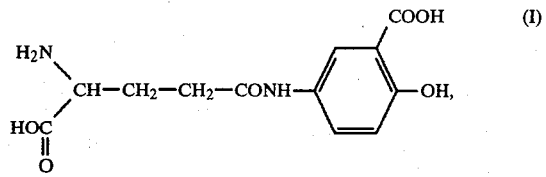

an acid addition salt thereof, or an alkali metal or amine salt thereof.

* * * * *